(12) United States Patent
Georgescu et al.

(10) Patent No.: US 11,449,998 B2
(45) Date of Patent: Sep. 20, 2022

(54) PROCESSING OF HISTOLOGY IMAGES WITH A CONVOLUTIONAL NEURAL NETWORK TO IDENTIFY TUMORS

(71) Applicant: Leica Biosystems Imaging, Inc., Vista, CA (US)

(72) Inventors: Walter Georgescu, Vista, CA (US); Allen Olson, San Diego, CA (US); Bharat Annaldas, Vista, CA (US); Darragh Lawler, Dublin (IE); Kevin Shields, Newcastle (GB); Kiran Saligrama, San Diego, CA (US); Mark Gregson, Newcastle (GB)

(73) Assignee: Leica Biosystems Imaging, Inc., Vista, CA (US)

( * ) Notice: Subject to any disclaimer, the term of this patent is extended or adjusted under 35 U.S.C. 154(b) by 145 days.

(21) Appl. No.: 16/986,987

(22) Filed: Aug. 6, 2020

(65) Prior Publication Data

US 2020/0364867 A1  Nov. 19, 2020

Related U.S. Application Data

(63) Continuation of application No. 16/230,820, filed on Dec. 21, 2018, now Pat. No. 10,740,896.
(Continued)

(51) Int. Cl.
*G06T 7/00* (2017.01)
*G06K 9/00* (2022.01)
(Continued)

(52) U.S. Cl.
CPC ........ *G06T 7/0014* (2013.01); *G06K 9/00523* (2013.01); *G06K 9/00536* (2013.01);
(Continued)

(58) Field of Classification Search
CPC ......... G06T 7/0014; G06T 2207/20084; G06T 2207/30096; G06T 2207/30024;
(Continued)

(56) References Cited

U.S. PATENT DOCUMENTS 6,819,790 B2  11/2004  Suzuki et al.
9,739,783 B1  8/2017  Kumar et al.
(Continued)

FOREIGN PATENT DOCUMENTS

CN  106030608 A  10/2016
CN  111542830 A  8/2020
(Continued)

OTHER PUBLICATIONS

Janowczyk A, Madabhushi A. Deep learinging for digital pathology image analysis: A comprehensive tutorial with selected use cases. J Pathol Inform, 2016.*
(Continued)

*Primary Examiner* — John B Strege

(57) ABSTRACT

A convolutional neural network (CNN) is applied to identifying tumors in a histological image. The CNN has one channel assigned to each of a plurality of tissue classes that are to be identified, there being at least one class for each of non-tumorous and tumorous tissue types. Multi-stage convolution is performed on image patches extracted from the histological image followed by multi-stage transpose convolution to recover a layer matched in size to the input image patch. The output image patch thus has a one-to-one pixel-to-pixel correspondence with the input image patch such that each pixel in the output image patch has assigned to it one of the multiple available classes. The output image patches are then assembled into a probability map that can be co-rendered with the histological image either alongside it or over it as an overlay. The probability map can then be stored linked to the histological image.

20 Claims, 8 Drawing Sheets
(2 of 8 Drawing Sheet(s) Filed in Color)

Related U.S. Application Data

(60) Provisional application No. 62/611,915, filed on Dec. 29, 2017.

(51) Int. Cl.

| | |
|---|---|
| *G06N 3/08* | (2006.01) |
| *G06N 5/04* | (2006.01) |
| *G16H 30/20* | (2018.01) |
| *G06N 20/00* | (2019.01) |
| *G06K 9/62* | (2022.01) |
| *G06V 10/44* | (2022.01) |
| *G06V 20/69* | (2022.01) |

(52) U.S. Cl.
CPC ............ *G06K 9/6271* (2013.01); *G06N 3/08* (2013.01); *G06N 5/04* (2013.01); *G06N 20/00* (2019.01); *G06V 10/454* (2022.01); *G06V 20/698* (2022.01); *G16H 30/20* (2018.01); *G06T 2207/10056* (2013.01); *G06T 2207/20084* (2013.01); *G06T 2207/30024* (2013.01); *G06T 2207/30096* (2013.01)

(58) Field of Classification Search
CPC ...... G06T 2207/10056; G06K 9/00147; G06K 9/6271; G06K 9/4628; G06K 9/00536; G06K 9/00523; G06N 3/08; G06N 5/04; G06N 20/00; G16H 30/20
See application file for complete search history.

(56) References Cited

U.S. PATENT DOCUMENTS

| | | | |
|---|---|---|---|
| 10,049,450 | B2 | 8/2018 | Madabhushi et al. |
| 10,373,312 | B2 | 8/2019 | Abedini et al. |
| 10,460,211 | B2 | 10/2019 | Vanhoucke et al. |
| 2015/0051484 | A1 | 2/2015 | Liu et al. |
| 2015/0213302 | A1 | 7/2015 | Madabhushi et al. |
| 2016/0063724 | A1 | 3/2016 | Tunstall et al. |
| 2016/0086326 | A1 | 3/2016 | Raschke et al. |
| 2016/0253466 | A1 | 9/2016 | Agaian et al. |
| 2016/0321512 | A1 | 11/2016 | Sarachan et al. |
| 2017/0124415 | A1 | 5/2017 | Choi et al. |
| 2017/0372117 | A1 | 12/2017 | Bredno et al. |
| 2018/0114317 | A1 | 4/2018 | Song et al. |
| 2018/0130203 | A1 | 5/2018 | Abedini et al. |
| 2018/0232883 | A1 | 8/2018 | Sethi et al. |
| 2018/0263568 | A1 | 9/2018 | Yi et al. |
| 2019/0065817 | A1 | 2/2019 | Mesmakhosroshahi et al. |
| 2019/0147592 | A1 | 5/2019 | Yu |
| 2019/0183429 | A1 | 6/2019 | Sung et al. |
| 2020/0372635 | A1* | 11/2020 | Veidman ............... G06T 7/0012 |

FOREIGN PATENT DOCUMENTS

| | | |
|---|---|---|
| JP | 2021-509713 A | 4/2021 |
| WO | WO 2019/133538 A2 | 7/2019 |

OTHER PUBLICATIONS

Extended European Search Report for EP 18893447.5 dated Apr. 1, 2021.
Feng et al.,"Patch-based fully convolutional neural network with skip connections for retinal blood vessel segmentation," Sep. 17, 2017, IEEE International Conference on Image Processing (ICIP), pp. 1742-1746.
Geert et al., "A survey on deep learning in medical image analysis," retrieved on Jun. 4, 2017, pp. 1-38.
Ronneberger et al., U-Net: Convolutional Networks for Biomedical Image Segmentation, May 18, 2015, Computer Science Department and BIOSS Centre for Biological Signaling Studies, pp. 1-8.
Badrinarayanan et al., "SegNet: A Deep Convolutional Encoder-Decoder Architecture for Image Segmentation," Oct. 10, 2016, IEEE Transactions on Pattern Analysis and Machine Intelligence, pp. 2481-2495.
Araujo et al. "Classification of breast cancer histology images using Convolutional Neural Networks." 2017) PLOS ONE 12(6): e0'177544., Jun. 1, 2017 [online] [retrieved on Mar. 13, 2019 (Mar. 13, 2019)I Retrieved from the Internet <URL: https://doi.org/10.13711,iournal.pone.0177544>.
Bejnordi et al., "Context-aware stacked convolutional neural networks for classification of breast carcinomas in whole-slide histopathology images", arXiv:1705.03678v1 [cs.CV] (2017), in 14 pages.
Cruz-Roa et al., "Accurate and reproducible invasive breast cancer detection in whole-slide images: A Deep Learning approach for quantifying tumor extent", Sci Rep. (2017) 7:46450. doi: 10.1038/srep46450, in 14 pages.
Esteva et al., "Dermatologist-level classification of skin cancer with deep neural networks", Nature. (2017) 542 (7639):115-18. doi:10.1038/nature21056, in 12 pages.
Hou et al., "Patch-based convolutional neural network for whole slide tissue image classification", Proc IEEE Comput Soc Conf Comput Vis Pattern Recognit. Jun -Jul. 2016;2016:2424-2433.
International Search Report and Written Opinion dated Apr. 1, 2019 for related International Application No. PCT/US2018/067349, in 15 pages.
Jouppi et al., "In-datacenter performance analysis of a tensor processing unit", 44th International Symposium on Computer Architecture (ISCA), Toronto, Canada, Jun. 24, 28, 2017 (submitted Apr. 16, 2017), arXiv: 1704.04760 [cs. AR] (2017), in 17 pages.
Liu et al., "Detecting cancer metastases on gigapixel pathology images", arXiv: 1703.02442 [cs.CV] (2017), in 13 pages.
Shelhamer et al., "Fully convolutional networks for semantic segmentation", IEEE Trans Pattern Anal Mach Intell. ( 2017) 39(4):640-651. doi: 10.1109/TPAMI.2016.2572683, in 10 pages.
Simonyan et al., "Very deep convolutional networks for large-scale image recognition", arXiv: 1409.1556 [cs.CV] (2015), in 14 pages.
Srivastava et al., "Dropout: a simple way to prevent neural networks from overfitting", Journal of Machine Learning Research 15 (2014) 1929-1958, in 30 pages.
Vandenberghe et al., "Relevance of deep learning to facilitate the diagnosis of HER2 status in breast cancer", Sci Rep (2017) 7:45938. doi: 10.1038/srep45938, in 11 pages.
Wang et al., "Deep learning for identifying metastatic breast cancer", arXiv: 1606.05718v1 [q-bio.QM] (2016), in 6 pages.
Hattori et al., "Tumor Tissue Identification Technology by Automatic Classification of Stained Images and Convolutional Neural Networks", Medical Imaging Technology; Nov. 29, 2017; vol. 35, No. 5, pp. 273-280.
Li et al., "Colorectal Polyp Segmentation Using A Fully Convolutional Neural Network", 2017 10th International Congress on Image and Signal Processing; BioMedical Engineering and Informatics (CISP-BMEI 2017); Oct. 2017 (document(s) showing well-known prior art).
First Australian Examination Report for Australian Patent Application No. 2018394106 dated Jan. 29, 2021 in 3 pages.
Second Australian Examination Report for Australian Patent Application No. 2018394106 dated Jul. 30, 2021 in 5 pages.
Third Australian Examination Report for Australian Patent Application No. 2018394106 dated Dec. 1, 2021 in 5 pages.
Notice of Allowance in Australian Application No. 2018394106 dated Jan. 31, 2022, in 3 pages.
Office Action in Chinese Application No. 201880084713.7 dated May 25, 2021, in 41 pages.
Office Action in Chinese Application No. 201880084713.7 dated Apr. 20, 2022, in 19 pages.
Office Action in Japanese Application No. 2020-536252 dated Jul. 6, 2021, in 11 pages.
Office Action in Japanese Application No. 2020-536252 dated Jan. 24, 2022, in 5 pages.
International Search Report on Patentability dated Nov. 27, 2019 for PCT/US2018/067349 in 3 pages.

(56) References Cited

OTHER PUBLICATIONS

European Communication dated Jun. 29, 2022, for Application No. 18893447.5, 7 pages.

* cited by examiner (TPU of Jouppi et al 2017)

PROCESSING OF HISTOLOGY IMAGES WITH A CONVOLUTIONAL NEURAL NETWORK TO IDENTIFY TUMORS

CROSS-REFERENCE TO RELATED APPLICATIONS

This application is a continuation of U.S. patent application Ser. No. 16/230,820, filed on Dec. 21, 2018, which claims priority to U.S. Provisional Patent Application No. 62/611,915, filed on Dec. 29, 2017, which are both hereby incorporated herein by reference as if set forth in full.

BACKGROUND

Field of the Invention

The present disclosure relates to processing of histology images with a convolutional neural network (CNN) in order to identify tumors.

Related Art

Cancer is the second leading cause of death in North American women. Of all types of cancer in women, breast cancer is the most common and the second leading cause of cancer death. Therefore, the accuracy of breast cancer treatment has a great impact on the lifespan and quality of life in the significant percentage of women that will be affected by breast cancer at some point in their lives.

Based on the expression of certain genes, breast cancers can be divided into different molecular subtypes. A commonly-used classification scheme is as follows:
1. Luminal A: ER+, PR+, HER2−
2. Luminal B: ER+, PR−, HER2+
3. Triple-Negative Breast Cancer (TNBC): ER−, PR−, HER2−
4. HER2-enriched: HER2+, ER−, PR−
5. Normal-like.

ER stands for estrogen receptor. PR stands for progesterone receptor. HER2 stands for human epidermal growth factor receptor 2.

Some of these subtypes such as Luminal A are hormone-receptor positive and may be treated with hormone therapy. Other breast cancers are HER2 positive and may be treated with drugs that target HER2 such as trastuzumab which has the trade name Herceptin (registered trade mark of F. Hoffmann-La Roche AG). It is important to determine if a breast cancer is ER, PR or HER2 positive, since cancers that are not positive will not respond to this type of treatment and need to be treated in another fashion. The determination of positivity has traditionally been made by a pathologist examining a histological sample on a glass slide under a microscope. On the glass slide, hormone-specific antibodies are applied using immunohistochemical (IHC) techniques to a formalin-fixed paraffin-embedded breast tissue section from the patient. After IHC staining is complete the immunoreactive tissue can be visualized under a microscope as a brown precipitate. The College of American Pathologists (CAP) recommends that all tumor-containing areas that stain positively should be evaluated to arrive at a percentage positivity. In order to improve the inter- and intra-observer reproducibility, the CAP guidelines recommend computing percentage positivity using image analysis. At present, pathologists performing image analysis have to outline the tumor areas manually, since percentage positivity has to be computed only over the tumor cell areas. The outlining process itself is tedious and error-prone and can lead to decreased reproducibility.

In principle, this problem is amenable to computer automation, either using conventional image processing methods of segmentation, boundary finding and so forth, or through artificial intelligence methods, in particular neural networks and deep learning. Nevertheless, in practice this problem has proved over many years to be incredibly difficult to computer automate to the required level of accuracy, i.e. as good as or better than a pathologist.

There have been attempts to use CNNs for image processing of histological images of breast cancer and other cancers.

Wang et al 2016 [1] describes a CNN approach to detect metastasis of breast cancer to the lymph nodes.

US2015213302A1 [2] describes how cellular mitosis is detected in a region of cancerous tissue. After training a CNN, classification is carried out based on an automated nuclei detection system which performs a mitotic count, which is then used to grade the tumor.

Hou et al 2016 [3] processes brain and lung cancer images. Image patches from whole slide images (WSIs) are used to make patch-level predictions given by patch-level CNNs.

Liu et al 2017 [4] processes image patches extracted from a gigapixel breast cancer histology image with a CNN to detect and localize tumors.

Bejnordi et al 2017 [5] applies two stacked CNNs to classify tumors in image patches extracted from WSIs of breast tissue stained with a hematoxylin and eosin (H&E) stain. We further note that Bejnordi et al also provides an overview of other CNN-based tumor classification methods applied to breast cancer samples (see references 10-13).

SUMMARY

According to one aspect of the disclosure, there is provided a method of identifying tumors in a histological image or set thereof, the method comprising:
  receiving a histological image or set thereof from a record stored in a data repository;
  extracting image patches from the histological image or set thereof, the image patches being area portions of the histological image or set thereof having a size defined by numbers of pixels in width and height;
  providing a convolutional neural network with a set of weights and a plurality of channels, each channel corresponding to one of a plurality of tissue classes to be identified, wherein at least one of the tissue classes represents non-tumorous tissue and at least one of the tissue classes represents tumorous tissue;
  inputting each image patch as an input image patch into the convolutional neural network;
  performing multi-stage convolution to generate convolution layers of ever decreasing dimensions up to and including a final convolution layer of minimum dimensions, followed by multi-stage transpose convolution to reverse the convolutions by generating deconvolution layers of ever increasing dimensions until a layer is recovered matched in size to the input image patch, each pixel in the recovered layer containing a probability of belonging to each of the tissue classes; and
  assigning a tissue class to each pixel of the recovered layer based on said probabilities to arrive at an output image patch.

The method may further comprise, after the assigning step, the step of: assembling the output image patches into a probability map for the histological image or set thereof.

The method may further comprise, after the assembling step, the step of: storing the probability map into the record in the data repository, so that the probability map is linked to the histological image or set thereof.

In our current implementation, in each successive convolution stage, as the dimensions decrease, the depth increases, so that the convolution layers are of ever increasing depth as well as ever decreasing dimensions, and in each successive transpose convolution stage, as the dimensions increase, the depth decreases, so that the deconvolution layers are of ever decreasing depth as well as ever increasing dimensions. The final convolution layer then has a maximum depth as well as minimum dimensions. Instead of the approach of successive depth increases and decreases through respectively the convolution and deconvolution stages, an alternative would be to design a neural network in which every layer except the input layer and the output layer has the same depth.

The method may further comprise: displaying on a display the histological image or set thereof with the probability map, e.g. overlaid thereon or alongside each other. The probability map can be used to determine which areas should be scored by whatever IHC scoring algorithms are to be used. The probability map can also be used to generate a set of contours around tumor cells which can be presented in the display, e.g. to allow a pathologist to evaluate the results generated by the CNN.

In certain embodiments, the convolutional neural network has one or more skip connections. Each skip connection takes intermediate results from at least one of the convolution layers of larger dimensions than the final convolution layer and subjects those results to as many transpose convolutions as needed, which may be none, one or more than one, to obtain at least one further recovered layer matched in size to the input image patch. These are then combined with the above-mentioned recovered layer prior to said step of assigning a tissue class to each pixel. A further processing step combines the recovered layer with each of the further recovered layers in order to recompute the probabilities, thereby taking account of the results obtained from the skip connections.

In certain embodiments, a softmax operation is used to generate the probabilities.

The image patches extracted from the histological image(s) may cover the whole area of the image(s). The patches may be non-overlapping image tiles or image tiles that overlap at their margins to aid stitching of the probability map. While each image patch should have a fixed number of pixels in width and height to be matched to the CNN, since the CNN will be designed to accept only a fixed size of pixel array, this does not mean that each image patch must correspond to the same physical area on the histological image, because pixels in the histological image may be combined into a lower resolution patch covering a larger area, e.g. each 2×2 array of neighboring pixels may be combined into one 'super'-pixel to form a patch with four times the physical area of a patch extracted at the native resolution of the histological image.

The method can be performed for prediction once the CNN has been trained. The purpose of the training is to assign suitable weight values for the inter-layer connections. For training, the records that are used will include ground truth data which assigns each pixel in the histological image or set thereof to one of the tissue classes. The ground truth data will be based on use of an expert clinician to annotate a sufficiently large number of images. Training is carried out by iteratively applying the CNN, where each iteration involves adjusting the weight values based on comparing the ground truth data with the output image patches. In our current implementation, the weights are adjusted during training by gradient descent.

There are various options for setting the tissue classes, but most if not all embodiments will have in common that a distinction will be made in the classes between non-tumorous and tumorous tissue. The non-tumorous tissue classes may include one, two or more classes. The tumorous tissue classes may also include one, two or more classes. For example, in our current implementation we have three tissue classes, one for non-tumorous tissue and two for tumorous tissue, wherein the two tumorous tissue classes are for invasive tumors and in situ tumors.

In some embodiments the CNN is applied to one histological image at a time. In other embodiments the CNN may be applied to a composite histological image formed by combining a set of histological images taken from differently stained, adjacent sections of a region of tissue. In still further embodiments, the CNN may be applied in parallel to each of the images of a set of images taken from differently stained, adjacent sections of a region of tissue.

With the results from the CNN, the method may be extended to include a scoring process based on the pixel classification and the tumors that are defined from that classification with reference to the probability map. For example, the method may further comprise: defining areas in the histological image that correspond to tumors according to the probability map; scoring each tumor according to a scoring algorithm to assign a score to each tumor; and storing the scores into the record in the data repository. The scoring thus takes place on the histological image, but is confined to those areas identified by the probability map as containing tumorous tissue.

The results may be displayed on a display to a clinician. Namely, a histological image can be displayed with its associated probability map, e.g. overlaid thereon or alongside each other. The tumor scores may also be displayed in some convenient manner, e.g. with text labels on or pointing to the tumors, or alongside the image.

The convolutional neural network may be a fully convolutional neural network.

A further aspect of the invention relates to a computer program product for identifying tumors in a histological image or set thereof, the computer program product bearing machine readable instructions for performing the above-described method.

A still further aspect of the invention relates to a computer apparatus for identifying tumors in a histological image or set thereof, the apparatus comprising:

an input operable to receive a histological image or set thereof from a record stored in a data repository;

a pre-processing module configured to extract image patches from the histological image or set thereof, the image patches being area portions of the histological image or set thereof having a size defined by numbers of pixels in width and height; and a convolutional neural network with a set of weights and a plurality of channels, each channel corresponding to one of a plurality of tissue classes to be identified, wherein at least one of the tissue classes represents non-tumorous tissue and at least one of the tissue classes represents tumorous tissue, the convolutional neural network being operable to:

receive as input each image patch as an input image patch;

perform multi-stage convolution to generate convolution layers of ever decreasing dimensions up to and including a final convolution layer of minimum dimensions, followed by multi-stage transpose convolution to reverse the convolutions by generating deconvolution layers of ever increasing dimensions until a layer is recovered matched in size to the input image patch, each pixel in the recovered layer containing a probability of belonging to each of the tissue classes; and assign a tissue class to each pixel of the recovered layer based on said probabilities to arrive at an output image patch.

The computer apparatus may further comprise: a post-processing module configured to assemble the output image patches into a probability map for the histological image or set thereof. Moreover, the computer apparatus may further comprise: an output operable to store the probability map into the record in the data repository, so that the probability map is linked to the histological image or set thereof. The apparatus may still further comprise: a display and a display output operable to transmit the histological image or set thereof and the probability map to the display such that the histological image is displayed with the probability map, e.g. overlaid thereon or alongside the probability map.

Another aspect of the invention is a clinical network comprising: a computer apparatus as described above; a data repository configured to store records of patient data including histological images or sets thereof; and network connections enabling transfer of patient data records or parts thereof between the computer apparatus and the data repository. The clinical network may additionally comprise an image acquisition apparatus, such as a microscope, operable to acquire histological images or sets thereof and to store them to records in the data repository.

It will be understood that in at least some embodiments the histological image(s) are digital representations of a two-dimensional image taken of a sectioned tissue sample by a microscope, in particular a light microscope, which may be a conventional optical microscope, a confocal microscope or any other kind of microscope suitable for obtaining histological images of unstained or stained tissue samples. In the case of a set of histological images, these may be of a succession of microscope images taken of adjacent sections (i.e. slices) of a region of tissue, wherein each section may be differently stained.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the following, the present invention will further be described by way of example only with reference to exemplary embodiments illustrated in the figures.

DETAILED DESCRIPTION

Figure 1A:
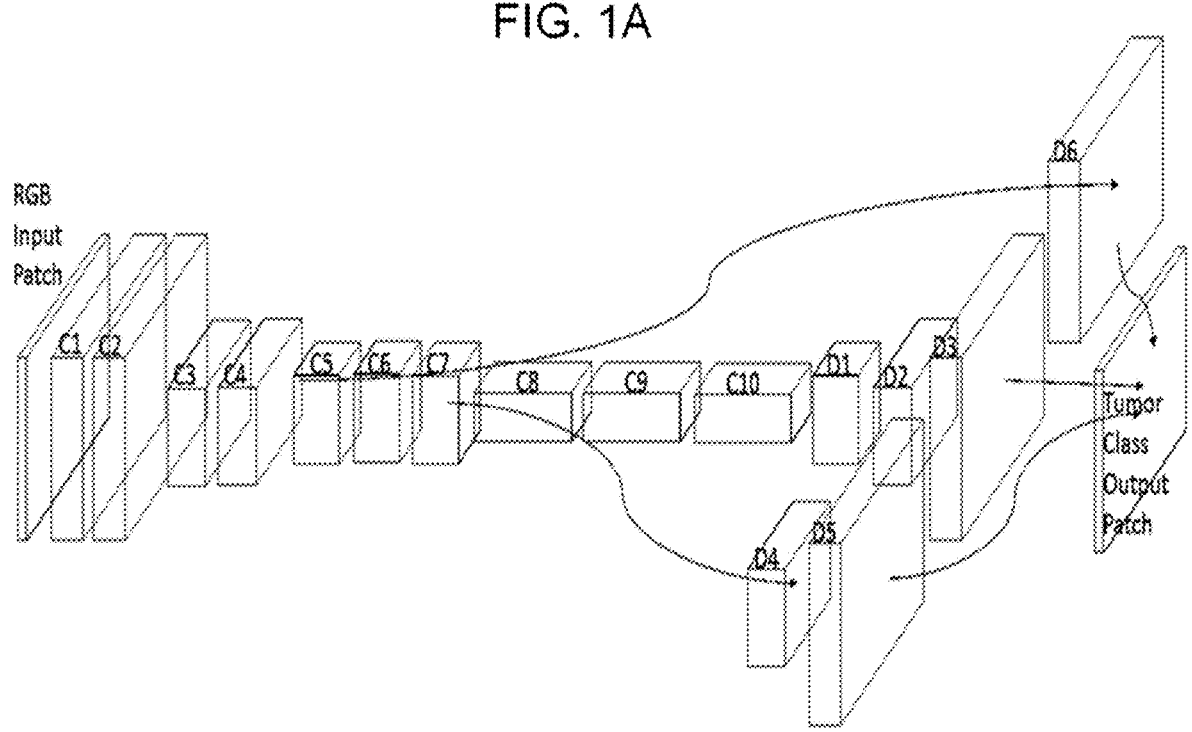
FIG. 1A is a schematic drawing of a neural network architecture according to one embodiment of the invention.

In the following detailed description, for purposes of explanation and not limitation, specific details are set forth in order to provide a better understanding of the present disclosure. It will be apparent to one skilled in the art that the present disclosure may be practiced in other embodiments that depart from these specific details.

We describe a computer-automated tumor finding method which detects and outlines invasive and in situ breast cancer cell nuclei automatically. The method is applied to a single input image, such as a WSI, or a set of input images, such as a set of WSIs. Each input image is a digitized, histological image, such as a WSI. In the case of a set of input images, these may be differently stained images of adjacent tissue sections. We use the term stain broadly to include staining with biomarkers as well as staining with conventional contrast-enhancing stains.

Since computer-automated outlining of tumors is much faster than manual outlining, it enables an entire image to be processed, rather than only manually-annotating selected extracted tiles from the image. The proposed automatic tumor outlining should thus enable pathologists to compute a positivity (or negativity) percentage over all the tumor cells in the image, which should result in more accurate and reproducible results.

The proposed computer-automated method for tumor finding, outlining and classifying uses a convolutional neural network (CNN) to find each nuclear pixel on the WSI and then to classify each such pixel into one of a non-tumor class and one of a plurality of tumor classes, in our current implementation breast tumor classes.

The neural network in our implementation is similar in design to the VGG-16 architecture available at www.robots.ox.ac.uk/~vgg/research/very_deep/ and described in Simonyan and Zisserman 2014 [6], the full contents of which are incorporated herein by reference.

The input image is a pathology image stained with any one of several conventional stains as discussed in more detail elsewhere in this document. For the CNN, image patches are extracted of certain pixel dimensions, e.g. 128×

128, 256×256, 512×512 or 1024×1024 pixels. It will be understood that the image patches can be of arbitrary size and need not be square, but that the number of pixels in the rows and columns of a patch conform to $2^n$, where n is a positive integer, since such numbers will generally be more amenable for direct digital processing by a suitable single CPU (central processing unit), GPU (graphics processing unit) or TPU (tensor processing unit), or arrays thereof.

We note that 'patch' is a term of art used to refer to an image portion taken from a WSI, typically with a square or rectangular shape. In this respect we note that a WSI may contain a billion or more pixels (gigapixel image), so image processing will typically be applied to patches which are of a manageable size (e.g. ca. 500×500 pixels) for processing by a CNN. The WSI will thus be processed on the basis of splitting it into patches, analyzing the patches with the CNN, then reassembling the output (image) patches into a probability map of the same size as the WSI. The probability map can then be overlaid, e.g. semi-transparently, on the WSI, or part thereof, so that both the pathology image and the probability map can be viewed together. In that sense the probability map is used as an overlay image on the pathology image. The patches analyzed by the CNN may be of all the same magnification, or may have a mixture of different magnifications, e.g. 5×, 20×, 50× etc. and so correspond to different sized physical areas of the sample tissue. By different magnifications, these may correspond to the physical magnifications with which the WSI was acquired, or effective magnifications obtained from digitally downscaling a higher magnification (i.e. higher resolution) physical image.

FIG. 1A is a schematic drawing of our neural network architecture. Layers C1, C2 . . . C10 are convolutional layers. Layers D1, D2, D3, D4, D5 and D6 are transpose convolution (i.e. deconvolutional) layers. The lines interconnecting certain layers indicate skip connections between convolutional, C, layers and deconvolutional, D, layers. The skip connections allow local features from larger dimension, shallower depth layers (where "larger" and "shallow" mean a convolutional layer of lower index) to be combined with the global features from the last (i.e. smallest, deepest) convolutional layer. These skip connections provide for more accurate outlines. Maxpool layers, each of which is used to reduce the width and height of the patch by a factor of 2, are present after layers C2, C4 and C7, but are not directly shown in the schematic, although they are shown by implication through the consequential reducing size of the patch. In some implementations of our neural network the maxpool layers are replaced with 1×1 convolutions resulting in a fully convolutional network.

The convolutional part of the neural network has the following layers in sequence: input layer (RGB input image patch); two convolutional layers, C1, C2; a first maxpool layer (not shown); two convolutional layers C3, C4; a second maxpool layer (not shown); three convolutional layers, C5, C6, C7, and a third maxpool layer (not shown). The output from the second and third maxpool layers is connected directly to deconvolutional layers using skip connections in addition to the normal connections to layers C5 and C8 respectively.

The final convolutional layer, C10, the output from the second maxpool layer (i.e. the one after layer C4) and the output from the third maxpool layer (i.e. the one after layer C7), are then each connected to separate sequences of "deconvolution layers" which upscale them back to the same size as the input (image) patch, i.e. convert the convolutional feature map to a feature map which has the same width and height as the input image patch and a number of channels (i.e. number of feature maps) equal to the number of tissue classes to be detected, i.e. a non-tumorous type and one or more tumor types. For the second maxpool layer, we see a direct link to the layer D6 since only one stage of deconvolution is needed. For the third maxpool layer, two stages of deconvolution are needed, via intermediate deconvolution layer D4, to reach layer D5. For the deepest convolutional layer C10, three stages of deconvolution are needed, via D1 and D2 to layer D3. The result is three arrays D3, D5, D6 of equal size to the input patch.

A simplified, albeit probably less-well performing, version of what is illustrated in FIG. 1A could omit the skip connections, in which case layers D4, D5 and D6 would not be present and the output patch would be computed solely from layer D3.

Figure 1B:
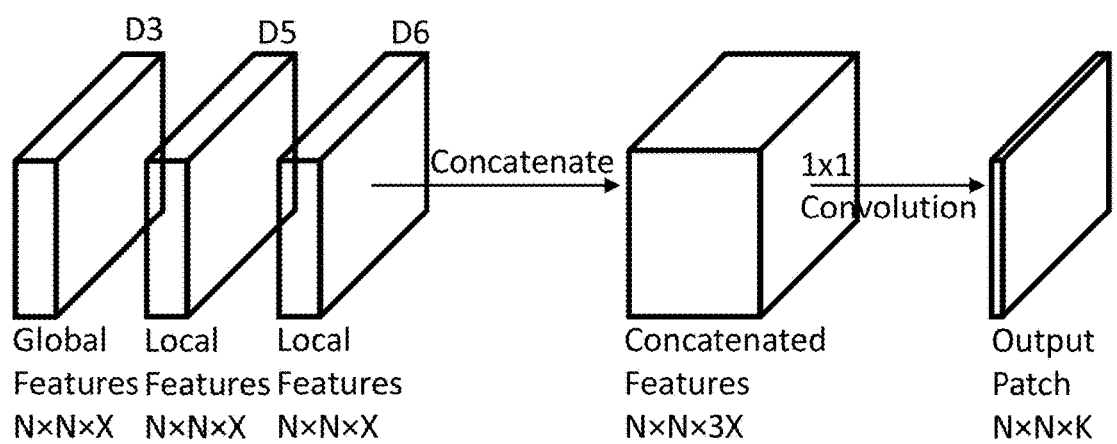
FIG. 1B shows how within the neural network architecture of FIG. 1A global and local feature maps are combined to generate a feature map that predicts an individual class for each pixel in an input image patch.

FIG. 1B shows in more detail how the final steps in the neural network architecture of FIG. 1A are carried out. Namely, global feature map layer D3 and local feature map layers D5, D6 are combined to generate a feature map that predicts an individual class for each pixel of the input image patch. Specifically, FIG. 1B shows how the final three transpose convolution layers D3, D5, D6 are processed to the tumor class output patch.

We now discuss how the above-described approach differs from a known CNN used currently in digital pathology. This known CNN assigns one class selected from multiple available classes to each image patch. Examples of such type of CNN are in the papers by Wang et al 2016 [1], Liu et al 2017 [4], Cruz-Roa et al 2017 [8] and Vandenberghe et al 2017 [9]. However, what we have just described is that, within a given image patch, one class selected from multiple available classes is assigned to each and every pixel. Therefore, instead of generating a single class label for each image patch, our neural network outputs a class label for each individual pixel of a given patch. Our output patch has a one-to-one pixel-to-pixel correspondence with the input patch such that each pixel in the output patch has assigned to it one of the multiple available classes (non-tumor, tumor 1, tumor 2, tumor 3 etc.).

In such known CNNs [1, 4, 8, 9], to assign a single class to each patch, a series of convolutional layers is employed followed by one or several fully connected layers, followed by an output vector which has as many values as there are classes to detect. The predicted class is determined by the location of the maximum value in the output vector.

To predict the class of individual pixels, our CNN uses a different architecture following the convolutional layers. Instead of a series of fully connected layers, we follow the convolutional layers with a series of transpose convolutional layers. The fully connected layers are removed from this architecture. Each transpose layer doubles the width and height of the feature maps while at the same time halving the number of channels. In this manner, the feature maps are upscaled back to the size of the input patch.

In addition, to improve the prediction, we use skip connections as described in Long et al 2015 [10], the full contents of which is incorporated herein by reference.

The skip connections use shallower features to improve the coarse predictions made by upscaling from the final convolutional layer C10. The local features from the skip connections contained in layers D5 and D6 of FIG. 1A are concatenated with the features generated by upscaling the global features contained in layer D3 of FIG. 1A from the final convolutional layer. The global and local feature layers D3, D5 and D6 are then concatenated into a combined layer as shown in FIG. 1B.

From the concatenated layer of FIG. 1B (or alternatively directly from the final deconvolutional layer D3 in the case that skip connections are not used), the number of channels is reduced to match the number of classes by a 1×1 convolution of the combined layer. A softmax operation on this classification layer then converts the values in the combined layer into probabilities. The output patch layer has size N×N×K, where N is the width and height in pixels of the input patches and K is the number of classes that are being detected. Therefore, for any pixel P in the image patch there is an output vector V of size K. A unique class can then be assigned to each pixel P by the location of the maximum value in its corresponding vector V.

The CNN thus labels each pixel as non-cancerous or belonging to one or more of several different cancer (tumor) types. The cancer of particular interest is breast cancer, but the method is also applicable to histology images of other cancers, such as cancer of the bladder, colon, rectum, kidney, blood (leukemia), endometrium, lung, liver, skin, pancreas, prostate, brain, spine and thyroid.

To the best of our knowledge this is the first time such an approach has been used in CNNs for the outlining and classification of breast cancer. We have determined that there is a performance improvement of this approach compared with previous computer-automated methods we are aware of, since the outlines are closer to those drawn by a pathologist, which are taken as the ground truth.

Our specific neural network implementation is configured to operate on input images having certain fixed pixel dimensions. Therefore, as a preprocessing step, both for training and prediction, patches are extracted from the WSI which have the desired pixel dimensions, e.g. N×N×n pixels, where n=3 in the case that each physical location has three pixels associated with three primary colors—typically RGB, when the WSI is a color image acquired by a conventional visible light microscope. (As mentioned further below 'n' may be 3 times the number of composited WSIs in the case the two or more color WSIs are combined.) Moreover 'n' would have a value of one in the case of a single monochrome WSI. To make training faster the input patches are also centered and normalized at this stage.

Our preferred approach is to process the entire WSI, or at least the entire area of the WSI which contains tissue, so the patches in our case are tiles that cover at least the entire tissue area of the WSI. The tiles may be abutting without overlap, or have overlapping edge margin regions of for example 1, 2, 3, 4, 5, 6, 7, 8, 9 or 10 pixels wide so that the output patches of the CNN can be stitched together taking account of any discrepancies. Our approach can however, if desired, also be applied to a random sample of patches over the WSI which are of the same or different magnification, as in the prior art, or as might be carried out by a pathologist.

Our neural network is similar in design to the VGG-16 architecture of Simonyan and Zisserman 2014 [6]. It uses very small 3×3 kernels in all convolutional filters. Max pooling is performed with a small 2×2 window and stride of 2. In contrast to the VGG-16 architecture, which has a series of fully connected layers after the convolutional layers, we follow the convolution layers with a sequence of "deconvolutions" (more accurately transpose convolutions) to generate segmentation masks. This type of upsampling for semantic segmentation has previously been used for natural image processing by Long et al 2015 [10], the full contents of which are incorporated herein by reference.

Each deconvolutional layer enlarges the input feature map by a factor of two in the width and height dimensions. This counteracts the shrinking effect of the maxpool layers and results in class feature maps of the same size as the input images. The output from each convolution and deconvolutional layer is transformed by a non-linear activation layer. At present, the non-linear activation layers use the rectifier function $ReLU(x)=\max(0,x)$. Different activation functions may be used, such as RELU, leaky RELU, ELU, etc. as desired.

The proposed method can be applied without modification to any desired number of tissue classes. The constraint is merely the availability of suitable training data which has been classified in the manner that it is desired to replicate in the neural network. Examples of further breast pathologies are invasive lobular carcinoma or invasive ductal carcinoma, i.e. the single invasive tumor class of the previous example can be replaced with multiple invasive tumor classes.

A softmax regression layer (i.e. multinomial logistic regression layer) is applied to each of the channel patches to convert the values in the feature map to probabilities.

After this final transformation by the softmax regression, a value at location location (x, y) in a channel C in the final feature map contains the probability, P(x, y), that the pixel at location location (x, y) in the input image patch belongs to the tumor type detected by channel C.

It will be appreciated that the number of convolution and deconvolution layers can be increased or decreased as desired and subject memory limitations of the hardware running the neural network.

We train the neural network using mini-batch gradient descent. The learning rate is decreased from an initial rate of 0.1 using exponential decay. We prevent neural network overfitting by using the "dropout" procedure described by Srivastava et al 2014 [2017], the full contents of which are incorporated herein by reference. Training the network may be done on a GPU, CPU or a FPGA using any one of several available deep learning frameworks. For our current implementation, we are using Google Tensorflow, but the same neural network could have been implemented in another deep learning framework such as Microsoft CNTK.

The neural network outputs probability maps of size N×N×K, where N is the width and height in pixels of the input patches and K is the number of classes that are being detected. These output patches are stitched back together into a probability map of size W×H×K, where W and H are the width and height of the original WSI before being split into patches.

The probability maps can then be collapsed to a W×H label image by recording the class index with maximum probability at each location (x, y) in the label image.

In its current implementation, our neural network assigns every pixel to one of three classes: non-tumor, invasive tumor and in situ tumor.

When multiple tumor classes are used, the output image can be post-processed into a more simple binary classification of non-tumor and tumor, i.e. the multiple tumor classes are combined. The binary classification may be used as an option when creating images from the base data, while the multi-class tumor classification is retained in the saved data.

While the above description of a particular implementation of our invention has concentrated on a specific approach using a CNN, it will be understood that our approach can be implemented in a wide variety of different types of convolutional neural network. In general any neural network that uses convolution to detect increasingly complex features and subsequently uses transpose convolutions ("deconvolutions") to upscale the feature maps back to the width and height of the input image should be suitable.

EXAMPLE 1

Figure 2:
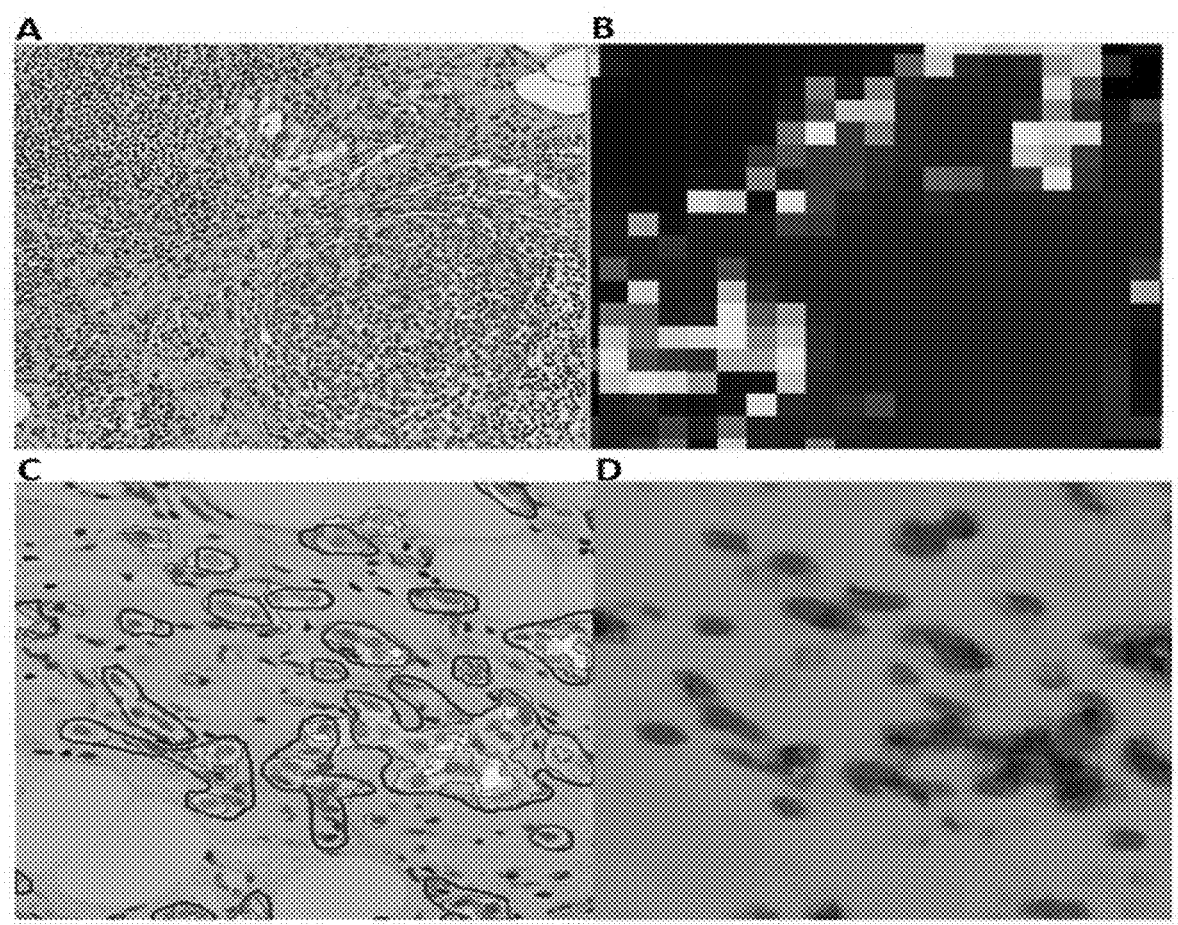
FIG. 2 is a color drawing showing the difference between patch-level predictions generated: by Liu et al (Tile A on the left is the raw image, Tile B on the right is the CNN prediction where dark red is the predicted tumor area); and by our predictions using the CNN of FIGS. 1A and 1B (Tile C on the left is the raw image with pathologist hand-annotation (red) and CNN predictions (pink and yellow), Tile D on the right is our CNN prediction where green is non-tumor, red (=pink in Tile C) is invasive tumor and blue (=yellow in Tile C) is non-invasive tumor).

FIG. 2 is in color and shows the difference between patch-level predictions such as those generated by Google's CNN solution for the Camelyon competition (Liu et al. 2017 [4]) and the pixel-level predictions generated by our CNN.

Figure 7:
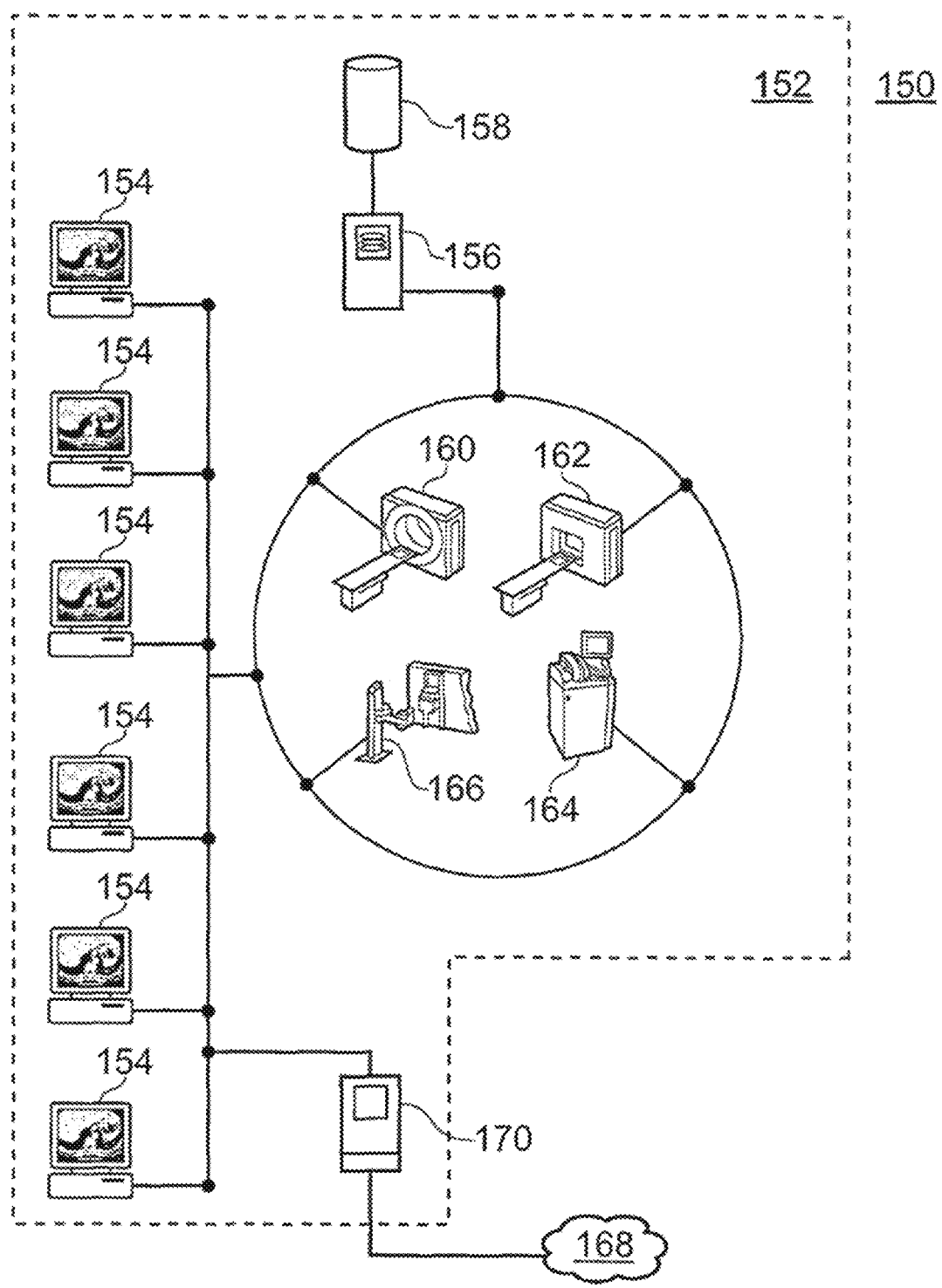
FIG. 7 shows an example computer network which can be used in conjunction with embodiments of the invention.

Tiles A and B in FIG. 2 are copied from FIG. 7 of Liu et al 2017 [4], whereas Tiles C and D are comparable tiles for an example according to our invention.

Tile A is a patch from an H&E-stained WSI in which the cluster of larger, dark purple cells in the bottom right quadrant is a tumor, while the smaller dark purple cells are lymphocytes.

Tile B is a tumor probability heatmap generated by the CNN of Liu et al 2017 [4] which the authors state accurately identifies the tumor cells, while ignoring the connective tissue and lymphocytes.

Tile C is a raw image patch from an example WSI to which the CNN method embodying the invention is applied. As well as the raw image, Tile C shows outlines drawn manually by a pathologist (solid red perimeter lines). In addition, with reference to Tile D, Tile C also shows results from our CNN method (first areas shaded pink with pink perimeter lines correspond to a first tumor type, i.e. the tumor type shown red in Tile D; second areas shaded yellow with pink perimeter lines correspond to a second tumor type, i.e. the tumor type shaded blue in Tile D).

Tile D is a tumor probability heatmap generated by our CNN. It can be seen how our approach of pixel-level prediction produces areas with smooth perimeter outlines. For our heatmap, different (arbitrarily chosen) colors indicate different classes, namely green for non-tumor, red for a first tumor type and blue for a second tumor type.

EXAMPLE 2

Figure 3:
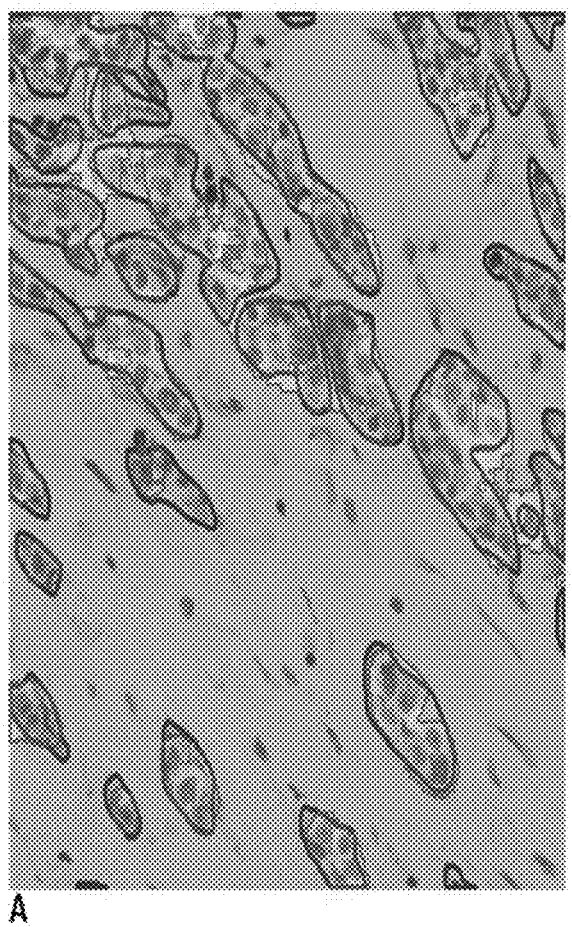
FIG. 3 is a color drawing showing an example of the input RGB image patch (Tile A on the left) and the final output tumor probability heat map (Tile B on the right). Tile A additionally shows the pathologist's manual outlining of invasive tumors (red outlines) and in addition overlays of our neural network's predictions (shaded pink and yellow areas) as separately shown in Tile B (in reddish-brown and blue respectively).
Figure 3:
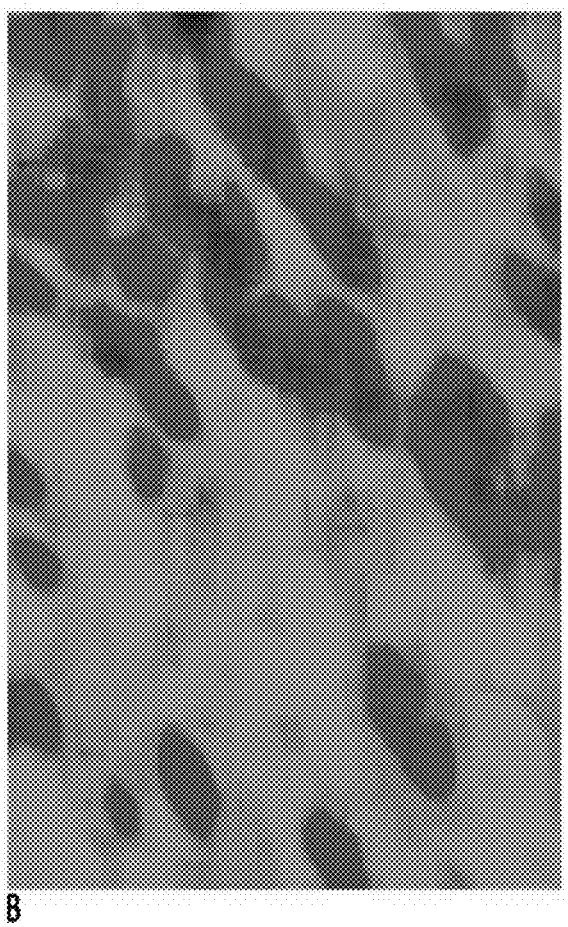

FIG. 3 is in color and shows an example of the input RGB image patch (Tile A on the left) and the final output tumor probability heat map (Tile B on the right).

Tile A additionally shows the pathologist's manual outlining of invasive tumors (red outlines) and in addition overlays of our neural network's predictions (shaded pink and yellow areas) as separately shown in Tile B.

Tile B is a tumor probability heatmap generated by our CNN. For our heatmap, different (arbitrarily chosen) colors indicate different classes, namely green for non-tumor, reddish-brown for invasive tumor (shown pink in Tile A), and blue for in situ tumor (shown yellow in Tile A). Once again, it can be seen how our approach of pixel-level prediction produces areas with smooth perimeter outlines. Moreover, it can be seen how the CNN predictions are compatible with the pathologist's manual marking. In addition, the CNN provides a further distinction between invasive and non-invasive (in situ) tissue which was not carried out by the pathologist, and is inherently part our multi-channel CNN design which can be programmed to and trained for classifying tissue into any number of different types as desired and clinically relevant.

Acquisition & Image Processing

The starting point of the method is that a tissue sample has been sectioned, i.e. sliced, and adjacent sections have been stained with different stains. The adjacent sections will have very similar tissue structure, since the sections are thin, but will not be identical, since they are of different layers.

For example, there could be 5 adjacent sections, each with a different stain, such as ER, PR, p53, HER2, H&E and Ki-67. A microscope image is then acquired of each section. Although the adjacent sections will have very similar tissue shapes, the stains will highlight different features, e.g. nucleus, cytoplasm, all features by general contrast enhancement etc.

The different images are then aligned, warped or otherwise pre-processed to map the coordinates of any given feature on one image to the same feature on the other images. The mapping will take care of any differences between the images caused by factors such as slightly different magnifications, orientation differences owing to differences in slide alignment in the microscope or in mounting the tissue slice on the slide, and so forth.

It is noted that with a coordinate mapping between different WSIs of a set comprising differently stained adjacent sections, the WSIs can be merged into a single composite WSI from which composite patches may be extracted for processing by the CNN, where such composite patches would have dimensions N×N×3m, where 'm' is the number of composited WSIs forming the set.

Some standard processing of the images is then carried out. These image processing steps may be carried out on the WSI level or at the level of individual image patches. The images may be converted from color to grayscale if the CNN is configured to operate on monochrome rather than color images. The images may be modified by applying a contrast enhancement filter. Some segmentation may then performed to identify common tissue areas in the set of images or simply to reject background that does not relate to tissue. Segmentation may involve any or all of the following image processing techniques:

Variance based analysis to identify the seed tissue areas
Adaptive thresholding
Morphological operations (e.g. blob analysis)
Contour identification
Contour merging based on proximity heuristic rules
Calculation of invariant image moments
Edge extraction (e.g. Sobel edge detection)
Curvature flow filtering
Histogram matching to eliminate intensity variations between serial sections
Multi-resolution rigid/affine image registration (gradient descent optimizer)
Non-rigid deformation/transformation
Superpixel clustering It will also be understood that image processing steps of the above kind can be carried on the WSIs or on individual patches after patch extraction. In some cases, it may be useful to carry out the same type of image processing both before and after patch extraction. That is, some image processing may be done on the WSI before patch extraction and other image processing may be done on a patch after its extraction from the WSI.

These image processing steps are described by way of example and should not be interpreted as being in any way limitative on the scope of the invention. For example, the CNN could work directly with color images if sufficient processing power is available.

Training & Prediction

Figure 4:
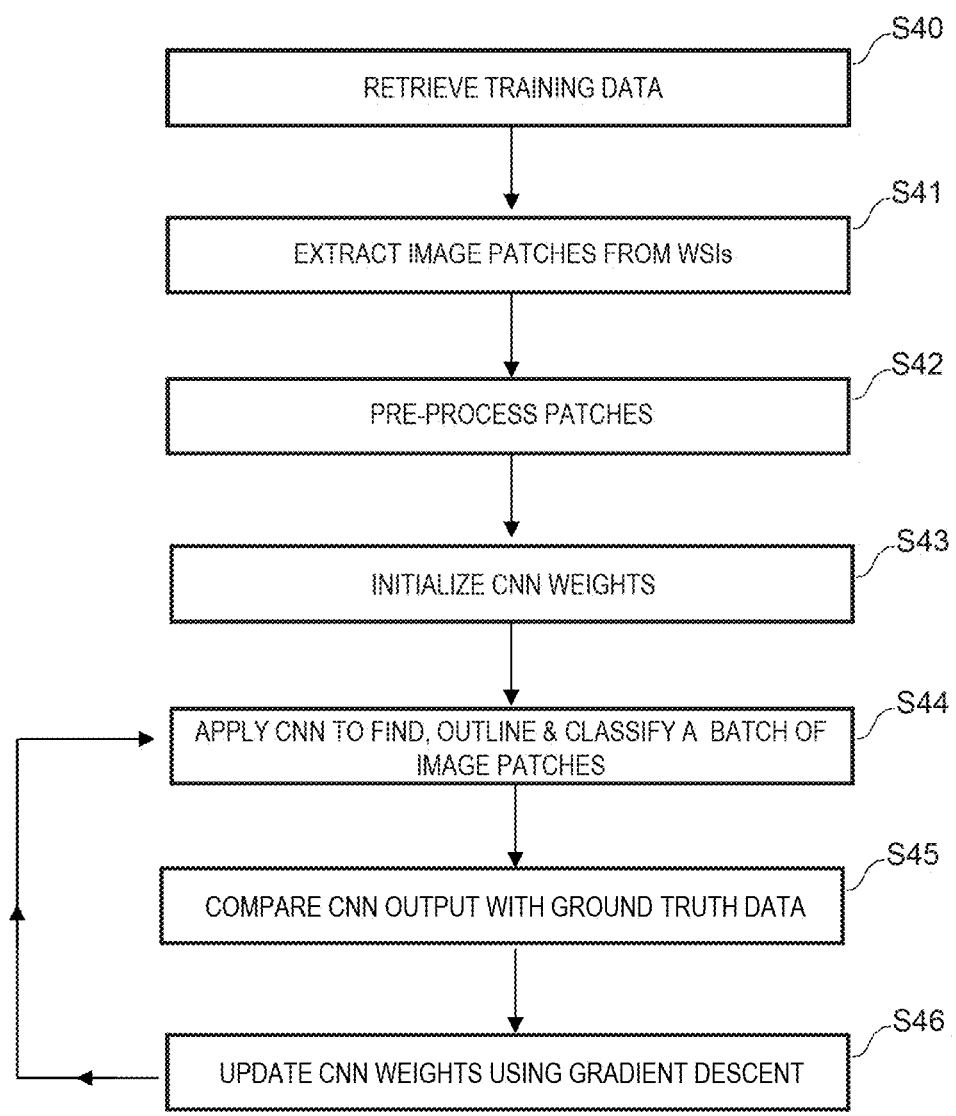
FIG. 4 is a flow diagram showing the steps involved in training the CNN.

FIG. 4 is a flow diagram showing the steps involved in training the CNN.

In Step S40, training data is retrieved containing WSIs for processing which have been annotated by a clinician to find, outline and classify tumors. The clinician's annotations represent the ground truth data.

In Step S41, the WSIs are broken down into image patches, which are the input image patches for the CNN. That is, image patches are extracted from the WSI.

In Step S42, the image patches are pre-processed as described above. (Alternatively, or in addition, the WSIs could be pre-processed as described above prior to Step S41.)

In Step S43, initial values are set for the CNN weights, i.e. the weights between layers.

In Step S44, each of a batch of input image patches is input into the CNN and processed to find, outline and classify the patches on a pixel-by-pixel basis as described further above with reference to FIGS. 1A and 1B. The term outline here is not necessarily strictly technically the right term to use, since our method identifies each tumor (or tumor type) pixel, so it is perhaps more accurate to say that the CNN determines tumor areas for each tumor type.

In Step S45, the CNN output image patches are compared with the ground truth data. This may be done on a per-patch basis. Alternatively, if patches have been extracted that cover the entire WSI, then this may be done at the WSI level, or in sub-areas of the WSI made up of a contiguous batch of patches, e.g. one quadrant of the WSI. In such variants, the output image patches can be reassembled into a probability map for the entire WSI, or contiguous portion thereof, and the probability map can be compared with the ground truth data both by the computer and also by a user visually if the probability map is presented on the display as a semi-transparent overlay to the WSI, for example.

In Step S46, the CNN then learns from this comparison and updates the CNN weights, e.g. using a gradient descent approach. The learning is thus fed back into repeated processing of the training data as indicated in FIG. 4 by the return loop in the process flow, so that the CNN weights can be optimized.

After training, the CNN can be applied to WSIs independently of any ground truth data, i.e. in live use for prediction.

Figure 5:
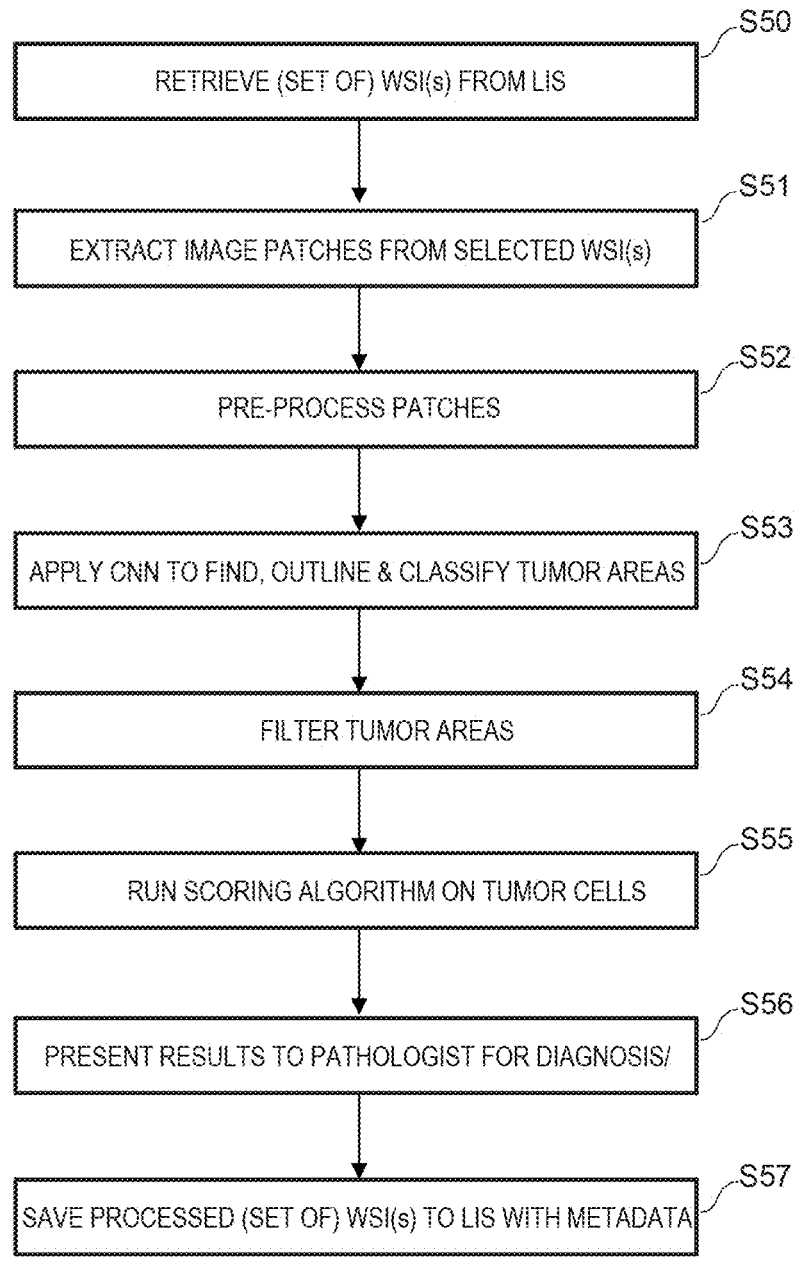
FIG. 5 is a flow diagram showing the steps involved in prediction using the CNN.

FIG. 5 is a flow diagram showing the steps involved in prediction using the CNN.

In Step S50, one or more WSIs are retrieved for processing, e.g. from a laboratory information system (LIS) or other histological data repository. The WSIs are pre-processed, for example as described above.

In Step S51, image patches are extracted from the or each WSI. The patches may cover the entire WSI or may be a random or non-random selection.

In Step S52, the image patches are pre-processed, for example as described above.

In Step S53, each of a batch of input image patches is input into the CNN and processed to find, outline and classify the patches on a pixel-by-pixel basis as described further above with reference to FIGS. 1A and 1B. The output patches can then be reassembled as a probability map for the WSI from which the input image patches were extracted. The probability map can be compared with the WSI both by the computer apparatus in digital processing and also by a user visually, if the probability map is presented on the display as a semi-transparent overlay on the WSI or alongside the WSI, for example.

In Step S54, the tumor areas are filtered excluding tumors that are likely to be false positives, for example areas that are too small or areas that may be edge artifacts.

In Step S55, a scoring algorithm is run. The scoring is cell-specific and the score may be aggregated for each tumor, and/or further aggregated for the WSI (or sub-area of the WSI).

In Step S56, the results are presented to a pathologist or other relevantly skilled clinician for diagnosis, e.g. by display of the annotated WSI on a suitable high-resolution monitor.

In Step S57, the results of the CNN, i.e. the probability map data and optionally also metadata relating to the CNN parameters together with any additional diagnostic information added by the pathologist, are saved in a way that is linked to the patient data file containing the WSI, or set of WSIs, that have been processed by the CNN. The patient data file in the LIS or other histological data repository is thus supplemented with the CNN results.

Computing Platforms

The proposed image processing may be carried out on a variety of computing architectures, in particular ones that are optimized for neural networks, which may be based on CPUs, GPUs, TPUs, FPGAs and/or ASICs. In some embodiments, the neural network is implemented using Google's Tensorflow software library running on Nvidia GPUs from Nvidia Corporation, Santa Clara, Calif., such as the Tesla K80 GPU. In other embodiments, the neural network can run on generic CPUs. Faster processing can be obtained by a purpose-designed processor for performing CNN calculations, for example the TPU disclosed in Jouppi et al 2017 [11], the full contents of which is incorporated herein by reference.

Figure 6:
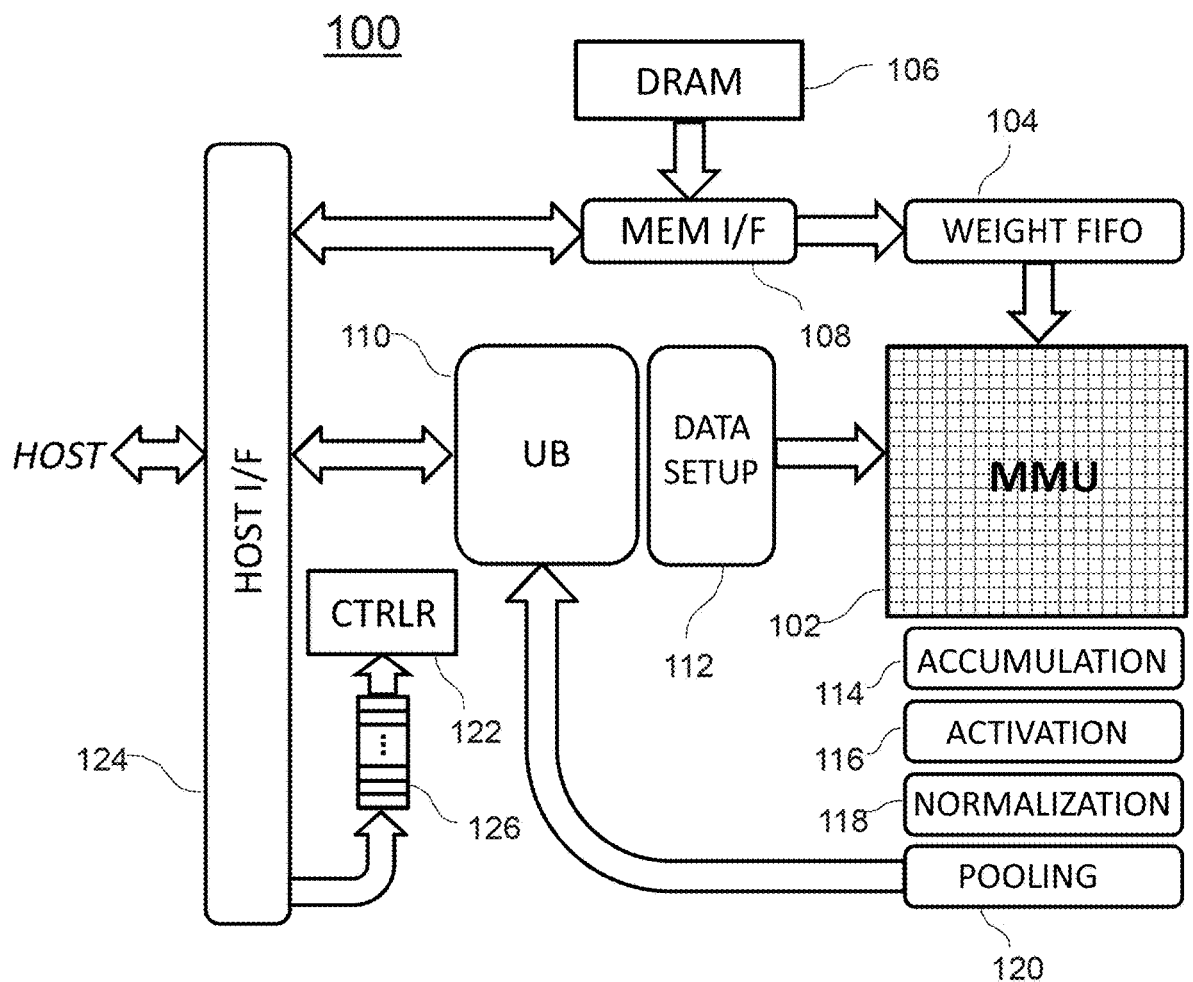
FIG. 6 is a block diagram of a TPU which may be used for performing the computations involved in implementing the neural network architecture of FIGS. 1A and 1B.

FIG. 6 shows the TPU of Jouppi et al 2017 [11], being a simplified reproduction of Jouppi's FIG. 1. The TPU 100 has a systolic matrix multiplication unit (MMU) 102 which contains 256×256 MACs that can perform 8-bit multiply-and-adds on signed or unsigned integers. The weights for the MMU are supplied through a weight FIFO buffer 104 that in turn reads the weights from a memory 106, in the form of an off-chip 8 GB DRAM, via a suitable memory interface 108. A unified buffer (UB) 110 is provided to store the intermediate results. The MMU 102 is connected to receives inputs from the weight FIFO interface 104 and the UB 110 (via a systolic data setup unit 112) and outputs the 16-bit products of the MMU processing to an accumulator unit 114. An activation unit 116 performs nonlinear functions on the data held in the accumulator unit 114. After further processing by a normalizing unit 118 and a pooling unit 120, the intermediate results are sent to the UB 110 for resupply to the MMU 102 via the data setup unit 112. The pooling unit 120 may perform maximum pooling (i.e. maxpooling) or average pooling as desired. A programmable DMA controller 122 transfers data to or from the TPU's host computer and the UB 110. The TPU instructions are sent from the host computer to the controller 122 via a host interface 124 and an instruction buffer 126.

It will be understood that the computing power used for running the neural network, whether it be based on CPUs, GPUs or TPUs, may be hosted locally in a clinical network, e.g. the one described below, or remotely in a data center.

The proposed computer-automated method operates in the context of a laboratory information system (LIS) which in turn is typically part of a larger clinical network environment, such as a hospital information system (HIS) or picture archiving and communication system (PACS). In the LIS, the WSIs will be retained in a database, typically a patient information database containing the electronic medical records of individual patients. The WSIs will be taken from stained tissue samples mounted on slides, the slides bearing printed barcode labels by which the WSIs are tagged with suitable metadata, since the microscopes acquiring the WSIs are equipped with barcode readers. From a hardware perspective, the LIS will be a conventional computer network, such as a local area network (LAN) with wired and wireless connections as desired.

FIG. 7 shows an example computer network which can be used in conjunction with embodiments of the invention. The network 150 comprises a LAN in a hospital 152. The hospital 152 is equipped with a number of workstations 154 which each have access, via the local area network, to a hospital computer server 156 having an associated storage device 158. A LIS, HIS or PACS archive is stored on the storage device 158 so that data in the archive can be accessed from any of the workstations 154. One or more of the workstations 154 has access to a graphics card and to software for computer-implementation of methods of generating images as described hereinbefore. The software may be stored locally at the or each workstation 154, or may be stored remotely and downloaded over the network 150 to a workstation 154 when needed. In other example, methods embodying the invention may be executed on the computer server with the workstations 154 operating as terminals. For example, the workstations may be configured to receive user input defining a desired histological image data set and to display resulting images while CNN analysis is performed elsewhere in the system. Also, a number of histological and other medical imaging devices 160, 162, 164, 166 are connected to the hospital computer server 156. Image data collected with the devices 160, 162, 164, 166 can be stored directly into the LIS, HIS or PACS archive on the storage device 156. Thus histological images can be viewed and processed immediately after the corresponding histological image data are recorded. The local area network is connected to the Internet 168 by a hospital Internet server 170, which allows remote access to the LIS, HIS or PACS archive. This is of use for remote accessing of the data and for transferring data between hospitals, for example, if a patient is moved, or to allow external research to be undertaken.

Figure 8:
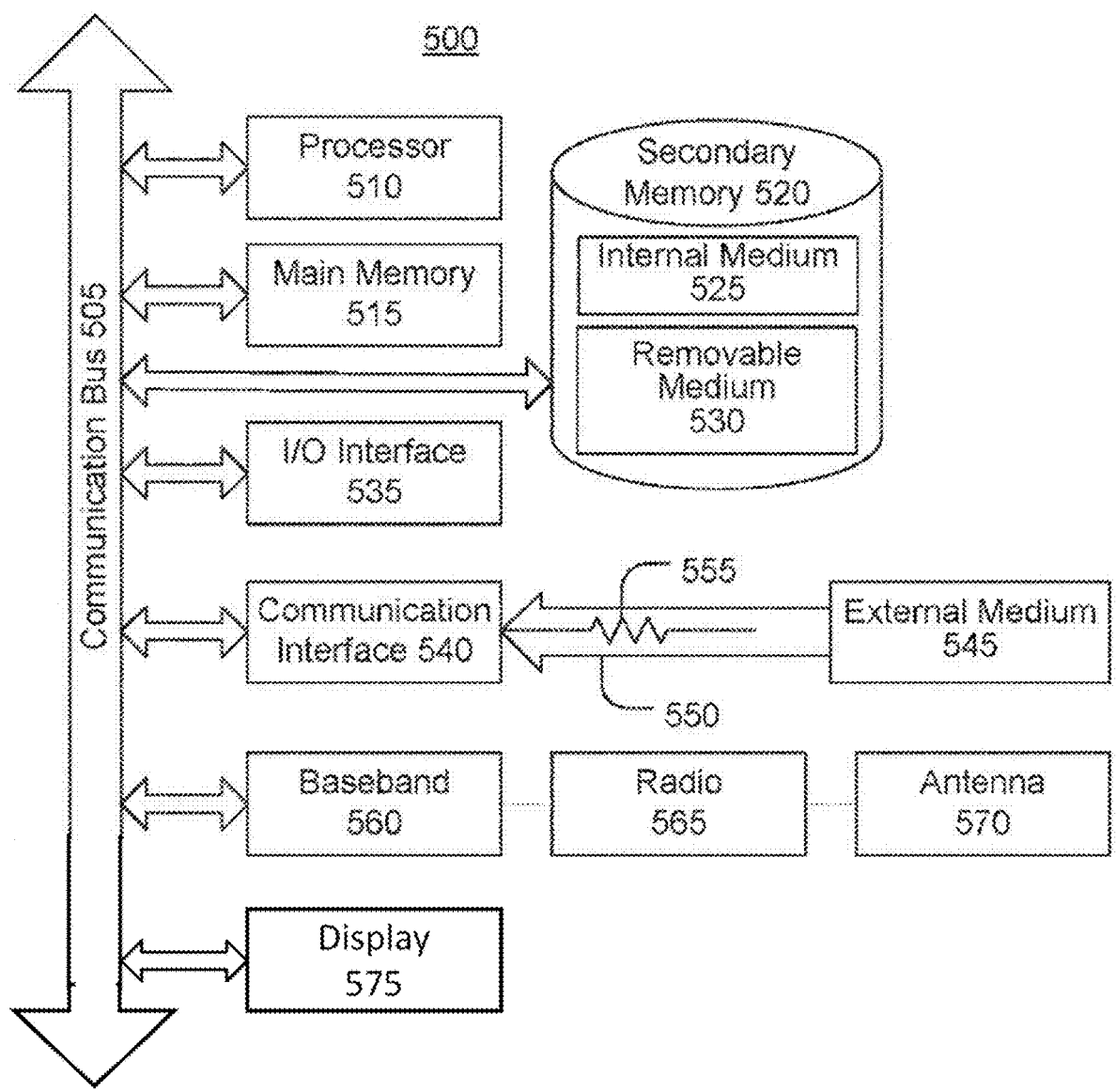
FIG. 8 is a block diagram of a computing apparatus that may be used for example as the host computer for the TPU of FIG. 6.

FIG. 8 is a block diagram illustrating an example computing apparatus 500 that may be used in connection with various embodiments described herein. For example, computing apparatus 500 may be used as a computing node in the above-mentioned LIS or PACS system, for example a host computer from which CNN processing is carried out in conjunction with a suitable GPU, or the TPU shown in FIG. 6.

Computing apparatus 500 can be a server or any conventional personal computer, or any other processor-enabled device that is capable of wired or wireless data communication. Other computing apparatus, systems and/or architectures may be also used, including devices that are not capable of wired or wireless data communication, as will be clear to those skilled in the art.

Computing apparatus 500 preferably includes one or more processors, such as processor 510. The processor 510 may be for example a CPU, GPU, TPU or arrays or combinations thereof such as CPU and TPU combinations or CPU and GPU combinations. Additional processors may be provided, such as an auxiliary processor to manage input/output, an auxiliary processor to perform floating point mathematical operations (e.g. a TPU), a special-purpose microprocessor having an architecture suitable for fast execution of signal processing algorithms (e.g., digital signal processor, image processor), a slave processor subordinate to the main processing system (e.g., back-end processor), an additional microprocessor or controller for dual or multiple processor systems, or a coprocessor. Such auxiliary processors may be discrete processors or may be integrated with the processor 510. Examples of CPUs which may be used with computing apparatus 500 are, the Pentium processor, Core i7 processor, and Xeon processor, all of which are available from Intel Corporation of Santa Clara, Calif. An example GPU which may be used with computing apparatus 500 is Tesla K80 GPU of Nvidia Corporation, Santa Clara, Calif.

Processor 510 is connected to a communication bus 505. Communication bus 505 may include a data channel for facilitating information transfer between storage and other peripheral components of computing apparatus 500. Communication bus 505 further may provide a set of signals used for communication with processor 510, including a data bus, address bus, and control bus (not shown). Communication bus 505 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, or standards promulgated by the Institute of Electrical and Electronics Engineers (IEEE) including IEEE 488 general-purpose interface bus (GPIB), IEEE 696/S-100, and the like.

Computing apparatus 500 preferably includes a main memory 515 and may also include a secondary memory 520. Main memory 515 provides storage of instructions and data for programs executing on processor 510, such as one or more of the functions and/or modules discussed above. It should be understood that computer readable program instructions stored in the memory and executed by processor 510 may be assembler instructions, instruction-set-architecture (ISA) instructions, machine instructions, machine dependent instructions, microcode, firmware instructions, state-setting data, configuration data for integrated circuitry, or either source code or object code written in and/or compiled from any combination of one or more programming languages, including without limitation Smalltalk, C/C++, Java, JavaScript, Perl, Visual Basic, .NET, and the like. Main memory 515 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Secondary memory 520 may optionally include an internal memory 525 and/or a removable medium 530. Removable medium 530 is read from and/or written to in any well-known manner. Removable storage medium 530 may be, for example, a magnetic tape drive, a compact disc (CD) drive, a digital versatile disc (DVD) drive, other optical drive, a flash memory drive, etc.

Removable storage medium 530 is a non-transitory computer-readable medium having stored thereon computer-executable code (i.e., software) and/or data. The computer software or data stored on removable storage medium 530 is read into computing apparatus 500 for execution by processor 510.

The secondary memory 520 may include other similar elements for allowing computer programs or other data or instructions to be loaded into computing apparatus 500. Such means may include, for example, an external storage medium 545 and a communication interface 540, which allows software and data to be transferred from external storage medium 545 to computing apparatus 500. Examples of external storage medium 545 may include an external hard disk drive, an external optical drive, an external magneto-optical drive, etc. Other examples of secondary memory 520 may include semiconductor-based memory such as programmable read-only memory (PROM), erasable programmable read-only memory (EPROM), electrically erasable read-only memory (EEPROM), or flash memory (block-oriented memory similar to EEPROM).

As mentioned above, computing apparatus 500 may include a communication interface 540. Communication interface 540 allows software and data to be transferred between computing apparatus 500 and external devices (e.g. printers), networks, or other information sources. For example, computer software or executable code may be transferred to computing apparatus 500 from a network server via communication interface 540. Examples of communication interface 540 include a built-in network adapter, network interface card (NIC), Personal Computer Memory Card International Association (PCMCIA) network card, card bus network adapter, wireless network adapter, Universal Serial Bus (USB) network adapter, modem, a network interface card (NIC), a wireless data card, a communications port, an infrared interface, an IEEE 1394 fire-wire, or any other device capable of interfacing system 550 with a network or another computing device. Communication interface 540 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 540 are generally in the form of electrical communication signals 555. These signals 555 may be provided to communication interface 540 via a communication channel 550. In an embodiment, communication channel 550 may be a wired or wireless network, or any variety of other communication links. Communication channel 550 carries signals 555 and can be implemented using a variety of wired or wireless communication means including wire or cable, fiber optics, conventional phone line, cellular phone link, wireless data communication link, radio frequency ("RF") link, or infrared link, just to name a few.

Computer-executable code (i.e., computer programs or software) is stored in main memory 515 and/or the secondary memory 520. Computer programs can also be received via communication interface 540 and stored in main memory 515 and/or secondary memory 520. Such computer programs, when executed, enable computing apparatus 500 to perform the various functions of the disclosed embodiments as described elsewhere herein.

In this document, the term "computer-readable medium" is used to refer to any non-transitory computer-readable storage media used to provide computer-executable code (e.g., software and computer programs) to computing apparatus 500. Examples of such media include main memory 515, secondary memory 520 (including internal memory 525, removable medium 530, and external storage medium 545), and any peripheral device communicatively coupled with communication interface 540 (including a network information server or other network device). These non-transitory computer-readable media are means for providing executable code, programming instructions, and software to computing apparatus 500. [90] In an embodiment that is implemented using software, the software may be stored on a computer-readable medium and loaded into computing apparatus 500 by way of removable medium 530, I/O interface 535, or communication interface 540. In such an embodiment, the software is loaded into computing apparatus 500 in the form of electrical communication signals 555. The software, when executed by processor 510, preferably causes processor 510 to perform the features and functions described elsewhere herein.

I/O interface 535 provides an interface between one or more components of computing apparatus 500 and one or more input and/or output devices. Example input devices include, without limitation, keyboards, touch screens or other touch-sensitive devices, biometric sensing devices, computer mice, trackballs, pen-based pointing devices, and the like. Examples of output devices include, without limitation, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), and the like.

Computing apparatus 500 also includes optional wireless communication components that facilitate wireless communication over a voice network and/or a data network. The wireless communication components comprise an antenna system 570, a radio system 565, and a baseband system 560. In computing apparatus 500, radio frequency (RF) signals are transmitted and received over the air by antenna system 570 under the management of radio system 565.

Antenna system 570 may comprise one or more antennae and one or more multiplexors (not shown) that perform a switching function to provide antenna system 570 with transmit and receive signal paths. In the receive path, received RF signals can be coupled from a multiplexor to a low noise amplifier (not shown) that amplifies the received RF signal and sends the amplified signal to radio system 565.

Radio system 565 may comprise one or more radios that are configured to communicate over various frequencies. In an embodiment, radio system 565 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 565 to baseband system 560.

If the received signal contains audio information, then baseband system 560 decodes the signal and converts it to an analog signal. Then the signal is amplified and sent to a speaker. Baseband system 560 also receives analog audio signals from a microphone. These analog audio signals are converted to digital signals and encoded by baseband system 560. Baseband system 560 also codes the digital signals for transmission and generates a baseband transmit audio signal that is routed to the modulator portion of radio system 565. The modulator mixes the baseband transmit audio signal with an RF carrier signal generating an RF transmit signal that is routed to antenna system 570 and may pass through a power amplifier (not shown). The power amplifier amplifies the RF transmit signal and routes it to antenna system 570 where the signal is switched to the antenna port for transmission.

Baseband system 560 is also communicatively coupled with processor 510, which may be a central processing unit (CPU). Processor 510 has access to data storage areas 515 and 520. Processor 510 is preferably configured to execute instructions (i.e., computer programs or software) that can be stored in main memory 515 or secondary memory 520. Computer programs can also be received from baseband processor 560 and stored in main memory 510 or in secondary memory 520, or executed upon receipt. Such computer programs, when executed, enable computing apparatus 500 to perform the various functions of the disclosed embodiments. For example, data storage areas 515 or 520 may include various software modules.

The computing apparatus further comprises a display 575 directly attached to the communication bus 505 which may be provided instead of or addition to any display connected to the I/O interface 535 referred to above.

Various embodiments may also be implemented primarily in hardware using, for example, components such as application specific integrated circuits (ASICs), programmable logic arrays (PLA), or field programmable gate arrays (FPGAs). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit, or step is for ease of description. Specific functions or steps can be moved from one module, block, or circuit to another without departing from the invention.

Moreover, the various illustrative logical blocks, modules, functions, and methods described in connection with the embodiments disclosed herein can be implemented or performed with a general purpose processor, a digital signal processor (DSP), an ASIC, FPGA, or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

A computer readable storage medium, as referred to herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Any of the software components described herein may take a variety of forms. For example, a component may be a stand-alone software package, or it may be a software package incorporated as a "tool" in a larger software product. It may be downloadable from a network, for example, a website, as a stand-alone product or as an add-in package for installation in an existing software application. It may also be available as a client-server software application, as a web-enabled software application, and/or as a mobile application.

Embodiments of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The illustrated flowcharts and block diagrams illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Apparatus and methods embodying the invention are capable of being hosted in and delivered by a cloud computing environment. Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

It will be clear to one skilled in the art that many improvements and modifications can be made to the foregoing exemplary embodiment without departing from the scope of the present disclosure.

REFERENCES

Wang, Dayong, Aditya Khosla, Rishab Gargeya, Humayun Irshad, and Andrew H Beck. 2016. "Deep Learning for Identifying Metastatic Breast Cancer." ArXiv Preprint ArXiv: 1606.05718.

US2015213302A1 (Case Western Reserve University)

Le Hou, Dimitris Samaras, Tahsin M. Kurc, Yi Gao, James E. Davis, and Joel H. Saltz "Patch-based Convolutional Neural Network for Whole Slide Tissue Image Classification", Proc. IEEE Comput Soc Conf Comput Vis Pattern Recognit. 2016, pages 2424-2433. doi:10.1109/CVPR Liu, Yun, Krishna Gadepalli, Mohammad Norouzi, George E Dahl, Timo Kohlberger, Aleksey Boyko, Subhashini Venugopalan, et al. 2017. "Detecting Cancer Metastases on Gigapixel Pathology Images." ArXiv Preprint ArXiv: 1703.02442.

Babak Ehteshami Bejnordi, Guido Zuidhof, Maschenka Balkenhol, Meyke Hermsen, Peter Bult, Bram van Ginneken, Nico Karssemeijer, Geert Litjens, Jeroen van der Laak "Context-aware stacked convolutional neural networks for classification of breast carcinomas in whole-slide histopathology images" 10 May 2017, ArXiv: 1705.03678v1

Simonyan and Zisserman. 2014. "Very Deep Convolutional Networks for Large-Scale Image Recognition." ArXiv Preprint ArXiv:1409.1556

Srivastava, Nitish, Geoffrey E Hinton, Alex Krizhevsky, Ilya Sutskever, and Ruslan Salakhutdinov. 2014. "Dropout: A Simple Way to Prevent Neural Networks from Overfitting." Journal of Machine Learning Research vol. 15(1): pages 1929-58.

Angel Cruz-Roa, Hannah Gilmore, Ajay Basavanhally, Michael Feldman, Shridar Ganesan, Natalie N.C. Shih, John Tomaszewski, Fabio A. Gonzalez & Anant Madabhushi. "A Deep Learning approach for quantifying tumor extent" Scientific Reports 7, Article number: 46450 (2017), doi:10.1038/srep46450

Michel E. Vandenberghe, Marietta L. J. Scott, Paul W. Scorer, Magnus Soderberg, Denis Balcerzak & Craig Barker. "Relevance of deep learning to facilitate the diagnosis of HER2 status in breast cancer". Scientific Reports 7, Article number: 45938 (2017), doi:10.1038/srep45938

Long, Jonathan, Evan Shelhamer, and Trevor Darrell. 2015. "Fully Convolutional Networks for Semantic Segmentation." In Proceedings of the IEEE Conference on Computer Vision and Pattern Recognition, pages 3431-40 Computer Vision and Pattern Recognition (cs.CV), arXiv: 1411.4038 [cs.CV]

Jouppi, Young, Patil et al "In-Datacenter Performance Analysis of a Tensor Processing Unit" 44th International Symposium on Computer Architecture (ISCA), Toronto, Canada, 24-28 Jun. 2017 (submitted 16 Apr. 2017), arXiv: 1704.04760 [cs.AR]

What is claimed is:

1. A method comprising using at least one hardware processor to, for each of one or more histological images of stained tissue samples:
receive the histological image;
extract a plurality of image patches from the histological image, wherein each of the plurality of image patches comprises a partial region of the histological image;
apply a convolutional neural network (CNN) to the plurality of image patches to:
classify each pixel of each of the plurality of image patches into one of a plurality of classes, wherein the plurality of classes comprises a non-tumor class representing an absence of tumor tissue and at least one tumor class representing tumor tissue, and
generate a plurality of output image patches based on classifying each pixel of each of the plurality of image patches into one of the plurality of classes, wherein a first pixel of an output image patch of the plurality of output image patches is classified into a first class of the plurality of classes and a second pixel of the output image patch is classified into a second class of the plurality of classes; and
generate a probability heatmap from the plurality of output image patches, wherein the probability heatmap is overlaid over the histological image, wherein the probability heatmap assigns a color to each pixel in the histological image based on the one class into which that pixel was classified.

2. The method of claim 1, further comprising using the at least one hardware processor to train the CNN using training data comprising histological images that have been annotated according to the plurality of classes.

3. The method of claim 2, wherein the training uses gradient descent.

4. The method of claim 1, wherein the at least one tumor class comprises a plurality of tumor classes, wherein each of the plurality of tumor classes represents a different type of tumor.

5. The method of claim 4, wherein the plurality of tumor classes comprises a first tumor class representing an invasive tumor and a second tumor class representing an in situ tumor.

6. The method of claim 1, wherein to classify each pixel of each of the plurality of image patches into one of the plurality of classes, the method further comprises using the at least one hardware processor to, for each pixel:
output, by the CNN, a vector of probabilities, wherein each probability in the vector is a probability that the pixel belongs to one of the plurality of classes; and
select a class of the plurality of classes into which the pixel is classified based on the vector of probabilities.

7. The method of claim 1, wherein the CNN comprises a plurality of convolutional layers and a plurality of deconvolutional layers.

8. The method of claim 7, wherein the CNN comprises a maxpool layer following at least one of the plurality of convolutional layers.

9. The method of claim 8, wherein the CNN comprises a skip connection between at least one maxpool layer and one of the plurality of deconvolutional layers.

10. The method of claim 9, wherein, for each of the plurality of image patches, the plurality of deconvolutional layers upscales a convolutional feature map of the image patch to a feature map with a same width and height as the image patch.

11. The method of claim 10, wherein each of the plurality of deconvolutional layers enlarges a width and height of an input feature map by a factor of two.

12. The method of claim 7, wherein to apply CNN, the method further comprises using the at least one hardware processor to, for each of the plurality of image patches:
concatenate two or more features maps, produced by different ones of the plurality of deconvolutional layers, into a combined feature map; and
convert the combined feature map into a probability map using a softmax operation, the probability map comprising a vector of probabilities for each pixel in the image patch, wherein each probability in each vector is a probability that the pixel belongs to one of the plurality of classes.

13. The method of claim 7, wherein an output of one or more of the plurality of convolutional layers or the plurality of deconvolutional layers is transformed by a rectifier function.

14. The method of claim 1, wherein none of the plurality of images patches overlap.

15. The method of claim 1, wherein two or more of the plurality of image patches overlap.

16. The method of claim 1, wherein to generate the probability heatmap, the method further comprises using the at least one hardware processor to, stitch the plurality of output image patches together, wherein each of the plurality of output image patches represents a probability map for one of the plurality of image patches.

17. The method of claim 1, wherein the plurality of image patches covers an entirety of the histological image.

18. The method of claim 1, wherein the plurality of image patches only covers a portion of the histological image.

19. A system comprising:
at least one hardware processor; and
one or more software modules that are configured to, when executed by the at least one hardware processor, for each of one or more histological images of stained tissue samples,
receive the histological image,
extract a plurality of image patches from the histological image, wherein each of the plurality of image patches comprises a partial region of the histological image;
apply a convolutional neural network (CNN) to the plurality of image patches to:
classify each pixel of each of the plurality of image patches into one of a plurality of classes, wherein the plurality of classes comprises a non-tumor class representing an absence of tumor tissue and at least one tumor class representing tumor tissue, and
generate a plurality of output image patches based on classifying each pixel of each of the plurality of image patches into one of the plurality of classes, wherein a first pixel of an output image patch of the plurality of output image patches is classified into a first class of the plurality of classes and a second pixel of the output image patch is classified into a second class of the plurality of classes; and
generate a probability heatmap from the plurality of output image patches, wherein the probability heatmap is overlaid over the histological image, wherein the probability heatmap assigns a color to each pixel in the histological image based on the one class into which that pixel was classified.

20. A non-transitory computer-readable medium having instructions stored thereon, wherein the instructions, when executed by a processor, cause the processor to, for each of one or more histological images of stained tissue samples:
receive the histological image;
extract a plurality of image patches from the histological image, wherein each of the plurality of image patches comprises a partial region of the histological image;
apply a convolutional neural network (CNN) to the plurality of image patches to:
classify each pixel of each of the plurality of image patches into one of a plurality of classes, wherein the plurality of classes comprises a non-tumor class representing an absence of tumor tissue and at least one tumor class representing tumor tissue, and
generate a plurality of output image patches based on classifying each pixel of each of the plurality of image patches into one of the plurality of classes, wherein a first pixel of an output image patch of the plurality of output image patches is classified into a first class of the plurality of classes and a second pixel of the output image patch is classified into a second class of the plurality of classes; and
generate a probability heatmap from the plurality of output image patches, wherein the probability heatmap is overlaid over the histological image, wherein the probability heatmap assigns a color to each pixel in the histological image based on the one class into which that pixel was classified.

* * * * *